United States Patent
Ochs et al.

(10) Patent No.: US 7,398,784 B2
(45) Date of Patent: Jul. 15, 2008

(54) INDICATOR DENTAL FLOSS

(75) Inventors: Harold Ochs, Flemington, NJ (US); John Chodzko, Helmetta, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 10/405,716

(22) Filed: Apr. 2, 2003

(65) Prior Publication Data
US 2003/0188762 A1 Oct. 9, 2003

Related U.S. Application Data

(63) Continuation of application No. 09/818,365, filed on Mar. 27, 2001, now abandoned.

(51) Int. Cl.
*A61C 15/00* (2006.01)
(52) U.S. Cl. .................................................. 132/321
(58) Field of Classification Search ................ 132/321, 132/329, 323; 424/486
See application file for complete search history.

(56) References Cited

U.S. PATENT DOCUMENTS

| | | | | |
|---|---|---|---|---|
| 3,943,949 A | * | 3/1976 | Ashton et al. | 132/321 |
| 5,209,251 A | * | 5/1993 | Curtis et al. | 132/321 |
| 5,220,932 A | * | 6/1993 | Blass | 132/321 |
| 5,340,581 A | * | 8/1994 | Tseng et al. | 424/401 |
| 5,357,989 A | * | 10/1994 | Gathani | 132/321 |
| 5,518,012 A | * | 5/1996 | Dolan et al. | 132/321 |
| 5,732,721 A | * | 3/1998 | Pelok | 132/321 |
| 5,875,797 A | * | 3/1999 | Chiang et al. | 132/321 |
| 5,906,834 A | * | 5/1999 | Tseng | 424/486 |
| 5,937,874 A | * | 8/1999 | Guay et al. | 132/321 |
| 5,941,256 A | | 8/1999 | Guay et al. | |
| 6,027,592 A | * | 2/2000 | Tseng et al. | 156/167 |
| 6,604,534 B2 | * | 8/2003 | Hill | 132/321 |
| 6,814,085 B2 | * | 11/2004 | Brattesani et al. | 132/321 |
| 2002/0144705 A1 | * | 10/2002 | Brattesani et al. | 132/321 |

FOREIGN PATENT DOCUMENTS

| | | | |
|---|---|---|---|
| GB | 2250817 A | * | 6/1992 |
| WO | WO 02/15814 A1 | | 2/2002 |
| WO | WO 02/053052 A2 | | 7/2002 |

OTHER PUBLICATIONS

EP Search Report dated Feb. 20, 2003 for corresponding EP application 02252187.6.
EP Communication dated Nov. 13, 2003 for corresponding EP application 02252187.6.

* cited by examiner

*Primary Examiner*—Robyn Doan

(57) ABSTRACT

A floss comprising: a fiber substrate; and a uniform coating comprising a colorant, wherein the color of the coating is different than the color of the fiber substrate is disclosed. The floss is useful as an indicator floss.

12 Claims, 1 Drawing Sheet

INDICATOR DENTAL FLOSS

CROSS REFERENCE TO RELATED APPLICATIONS

This is a continuation of application Ser. No. 09/818,365, filed Mar. 27, 2001 now abandoned.

FIELD OF THE INVENTION

This invention relates to a dental floss that changes color upon use, thereby providing a visual signal or clue to indicate the need to move to an area of the floss that has not been used. The floss comprises a fibrous substrate to which has been applied a coating composition that contains a colorant. Upon use, the colorant-containing coating is displaced or disrupted, revealing the floss substrate, which is different in color than the colorant.

BACKGROUND OF THE INVENTION

The use of dental floss is recommended by virtually all dental health practitioners. Flossing and brushing are the most common techniques for reducing bacteria in the mouth. The reduction of bacteria in the mouth is important because bacteria can cause cavities and gum disease. Dental flossing has been shown to remove bacteria in the interproximal as well as in the subgingival regions of the mouth.

In using dental floss, it is desirable not to use the same portion of floss between more than one pair of teeth. One reason for this is that floss wears during use. The floss may fray and shred, resulting in loose and broken filaments that can become stuck between teeth.

Another reason for not using the same portion of floss between more than one pair of teeth is that the use of floss between multiple pairs of teeth can carry food particles and bacteria from one site to another rather than out of the mouth.

Still another reason for using fresh portions of floss is for delivery of actives such as fluoride or flavors that freshen the mouth. Repeated use of the same region of the floss obviously reduces the ability of the floss to deliver desirable ingredients such as the above mentioned actives and flavors.

For the reasons mentioned above, dental professionals, such as hygienists, are taught to change floss positions when going from one pair of teeth to the next. However, most consumers do not practice this desirable technique. With ordinary flosses, it is sometimes impossible to tell where the floss has been used and where it hasn't. Therefore, there is a need for a floss that provides a visual signal or clue indicating the region(s) thereof which have been previously used.

One approach to providing an indication that a portion of floss has been used is illustrated in U.S. Pat. No. 5,941,256. The patent discloses a dental floss that is coated or provided with pigment-containing microcapsules on its surface. The pigment-containing microcapsules themselves are opaque. The opaque, pigment-containing microcapsules rupture during use of the floss, thereby releasing the pigment and giving a visual indication to the user that the area has been used. The pigment contained within the microcapsule has a color which contrasts with the color of the underlying floss substrate so that when the microcapsules are ruptured, the color of the released pigment is readily visible to the naked eye. The disadvantage of this microcapsule technology is that it is very expensive, thus rendering its use somewhat impractical from a commercial viewpoint.

Therefore, despite the disclosure of the prior art, there is a continuing need for a dental floss that provides a visual signal or clue indicating the region(s) thereof which have been previously used.

SUMMARY OF THE INVENTION

The present invention provides a dental floss including a fibrous substrate to which has been substantially uniformly applied a coating containing a colorant, wherein the color of the coating contrasts with or is different from the color of the fibrous substrate. The colorant is substantially uniformly present in the coating composition prior to and during its application to the floss substrate. The colorant is substantially uniformly present in the coating of the finished dental floss.

In one aspect of the present invention, there is provided a dental floss comprising a fiber substrate, said fiber substrate having a first color; said fiber substrate having a coating substantially uniformly applied thereto; said coating having a second color which substantially completely masks said first color; whereby when said floss is used to floss the teeth, said coating is disrupted to thereby reveal said first color, thereby providing the user with a visual indication that the floss has been so used.

In another aspect of the present invention, there is provided a dental floss comprising a fiber substrate, said fiber substrate having a first color; said fiber substrate having a first coating substantially uniformly applied thereto, said first coating being substantially insoluble; and a second coating substantially uniformly applied over said first insoluble coating, said second coating being a soluble coating and being adapted to substantially completely mask said first color, whereby when said floss is used to floss the teeth, said second coating is disrupted to thereby reveal an underlying color.

DETAILED DESCRIPTION OF THE INVENTION

Figure 1:
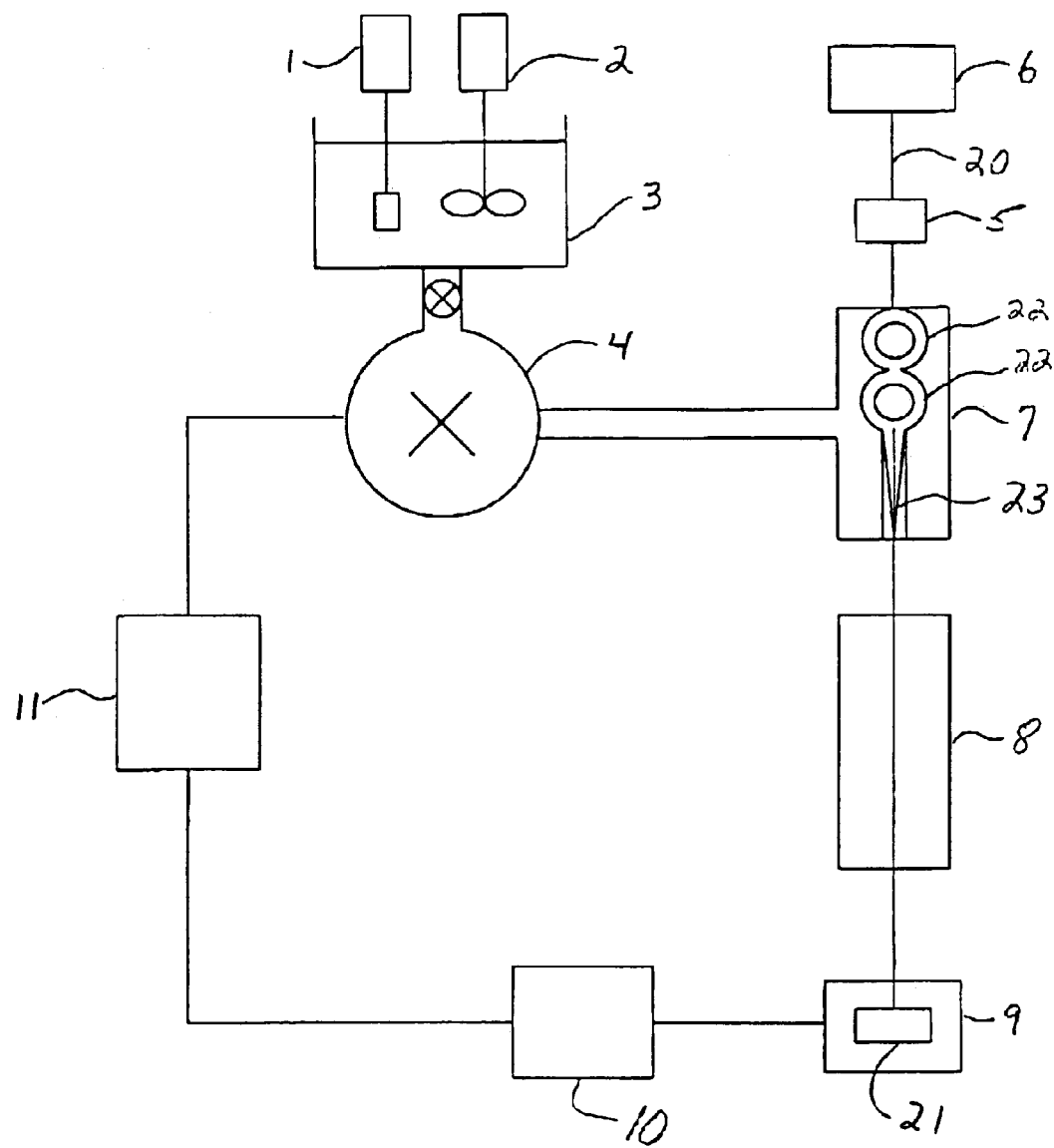
FIG. 1 is a schematic diagram of a process for making floss of the present invention.

The fibrous substrate comprising the dental floss of the present invention can be in the form of a monofilament or in the form of a yarn comprising a plurality of such monofilaments. A yarn comprising a plurality of monofilaments is sometimes referred to as a "multi-filament yarn".

A substrate in the form of a single monofilament (which is sometimes referred to as a "monofilament yarn") may be, e.g., circular or rectangular in cross section. A monofilament substrate in rectangular form typically has a width ranging from about 1.5 mm to 3 mm, a thickness ranging from about 0.02 mm to about 0.06 mm, and a denier ranging from about 600 to about 1800. In a specific example, a rectangular monofilament substrate has a width of about 1.8 mm, a thickness of about 0.05 mm, and a denier of about 940.

Substrates in the form of a multi-filament yarn are typically generally circular in cross section and typically have a denier ranging from about 400 to about 1400. The denier of the individual fibers typically ranges from about 1 to about 6, although other deniers may be used in some circumstances if desired.

The floss of the invention may also be made from a fiber substrate referred to as a psuedo-monofilament yarn. Pseudo-monofilament yarns are made by extruding bicomponent fibers typically having a core of one polymer and a sheath of a different polymer, then either partially or totally melting the sheaths of the fibers to bond or fuse the fibers, resulting in a monofilament appearance and feel. One example of a suitable bicomponent fiber for making pseudo-monofilament yarn comprises a core of nylon 6 with a sheath of Pebax® Brand polyether/amide copolymer. Other materials besides nylon can be used for the core of the bicomponent fibers and other polymeric materials besides polyether/amide copolymer may be used as the sheath material.

When the fiber substrate comprises a monofilament or a multifilament yarn, the yarns may be made of nylon 6-6, nylon 6, polypropylene, polyethylene, polyester, polytetrafluoroethylene, and the like materials. Combinations of such materials are also acceptable as long as they provide the floss with the strength and fray resistance needed in a dental floss.

The individual monofilaments comprising a multifilament yarn may, if desired, be air entangled. If the yarn is air entangled, the air entanglement nodes may be from about 1.25 cm to about 5.2 cm apart, preferably from 2 cm to 3 cm apart.

As is known in the art, the finished floss may be twisted. As a general rule, a finished twisted dental floss would have from about 1 to about 6 turns per 2.54 cm, preferably from about 1 to about 2 turns per 2.54 cm, and, more preferably, from about 1.2 to about 1.8 turns per 2.54 cm.

A coating composition containing a colorant that is different from or contrasts with the color of the floss substrate or underlying floss structure is applied substantially uniformly to the fiber substrate or underlying floss structure. As the consumer uses the floss, the colorant-containing coating is disturbed or disrupted, thus exposing the underlying substrate or floss structure which stands out due to its different or contrasting color.

In order to see the difference between a used area of floss and an unused area of floss, the floss must be substantially uniformly coated with a coating composition containing a colorant which contrasts with or is different in color than the underlying floss material. Further, the coating must be such that use of the floss causes a disturbance or disruption in the coating, thus exposing the underlying color. In one embodiment, this can be accomplished by having an insoluble coating composition which contains an insoluble colorant and which is soft enough to be displaced as the floss passes between tight spaces.

In another embodiment, a soluble coating containing a soluble colorant may be applied to a fiber substrate that is different in color than the colorant. When this floss is used, the coating is solubilized by saliva in the oral cavity, thus exposing the underlying floss substrate or structure.

Coating compositions for use in the present invention must reliably adhere the colorant to the surface of the floss, whether the fiber substrate is a multifilament, monofilament, or psuedo-monofilament yarn. The coating composition must have sufficient adherence to keep the colorant-containing coating on the surface of the floss during coating, winding, shipping and unwinding of the floss.

In the case of a multifilament floss, the coating serves to adhere the filaments together to prevent fraying and shredding of the floss during use. The coating must also be pliable at room temperature such that when used, the coating is displaced or disrupted. Preferably, an insoluble coating is used on a multifilament floss to hold the filaments together and to avoid dissolution of the coating in the saliva encountered in the oral cavity.

In one embodiment, two insoluble coatings are applied to the fiber substrate. In this embodiment, the second coating composition must have a lower melting point than the first coating composition. Preferably, the outer coating composition contains a colorant that is different in color than the underlying floss substrate carrying the first coating composition.

Suitable insoluble coatings include, but are not limited to, microcrystalline wax, beeswax, paraffin waxes, and low molecular weight polyethylenes. Typically, the insoluble coatings have melting temperatures ranging from 25° C. to 100° C., preferably from 35° C. to 80° C. The waxes may be combined with water insoluble colorants that are FD&C approved for use in the mouth. Suitable colorants include, but are not limited to, synthetically derived colorants such as FD&C Blue #1 Lake, FD&C Blue #2 Lake, FD&C Red #40 Lake, Erythrosin Lake, Amaranth Lake, Ponceau 4R Lake, Carmoisosine Lake, Carmine Lake and colorants generated by converting a naturally derived dye to an aluminum or calcium based salt. Natural colorants such as titanium dioxide and the like may also be used.

The coating composition applied to the fiber substrate may be a soluble coating, i.e., the coating is such that it tends to dissolve or disperse in saliva present in the oral cavity. Such soluble coatings include soluble waxes or the like, which include, but are not limited to, low molecular weight polyethylene glycols ("PEGs"), such as PEG 1000 and PEG 1450. Combinations of higher molecular weight PEGs and lower molecular weight PEGs, such as a mixture of PEG 3350 and PEG 1000 may be used. Blends of liquid PEG's with high molecular weight PEG's may also be used.

Soluble waxes may be used with appropriate colorants that must be substantially uniformly dispersed within the coating. Colorants used with soluble waxes should be water-soluble. When formulating colorants with PEG's it is necessary to keep the resultant average wax molecular weight low enough to maintain a soft wax and eliminate brittleness at room temperature. When the average molecular weight of the PEG or blends of PEG's is too high, the coating will tend to flake off the substrate during processing and during use. Flavors, sweeteners, surfactants, abrasives, anti-tartar agents, and actives such as fluoride salts, cetyl pyridinium chloride, etc. can be incorporated into the soluble coating compositions.

A soluble coating can be used by itself or as a second coating over an insoluble coating. One or both coatings can contain colorants, flavors, sweeteners, abrasives, anti-tartar agents, actives, such as fluoride salts, and like additives known in the art.

Additional components can be added to coatings for various benefits. These include flavor systems, such as spray dried flavors, flavor enhancers, and sweeteners, such as sodium saccharin. The amount of flavor added typically ranges from 10 percent to 25 percent, based on the total weight of the coating composition. The amount of sweetener typically ranges from 0.1 percent to 1 percent, based on the total weight is of the coating composition.

Other components can be added to coatings to assist in cleaning the teeth. These include actives including abrasives such as silica or di-calcium phosphate, and anti-tartar agents such as tetra-sodium-pyrophosphate. Where two coatings are used, actives are usually added in the second soluble coating to guarantee that a high percentage of the active will be released from the floss during use.

In formulating a coating, it is desirable to limit the amount of additives in the coating composition below about 30% by weight. Coating a floss substrate with a coating composition having an additive content above this amount may cause difficulty in achieving uniformity of coating and reduce the ability of the coating to adhere to the floss surface. Coatings containing high amounts of additives may tend to flake off during processing and during use of the final product.

The dental floss coating may be anhydrous or hydrous. When the coating is hydrous, the water is evaporated upon drying.

It is critical to the invention that the colorant used in any coating system is compatible and substantially uniformly dispersed, suspended, solubilized, emulsified or dissolved in the coating. The colorants may be dyes, pigments, inorganic colors, Lakes, particles, or other materials that exhibit color.

For soluble coatings, the amount of colorant may range from 0.1 percent to 5 percent, preferably from about 1 percent to about 3 percent by weight, based on the total weight of the coating composition.

For insoluble coatings, the amount of colorant may range from about 0.75 percent to about 5 percent, preferably from about 1 percent to about 3 percent by weight, based on the total weight of the coating composition.

In one embodiment, the floss contains a combination of two or more coatings of which at least the outer coating contains a colorant that is different in color than the underlying floss structure. Use of the floss disturbs the coating, resulting in a visual indication that the area of floss has been used.

The color difference between the coating containing the colorant and the fiber substrate must be sufficiently different to serve as a visual clue or indicator to the user. If the coating on the surface of the floss is too thin, the amount of colorant in the coating is too little, or the color variation between the substrate and coating is not readily apparent, the used area will not be readily discernable upon use. Also, if the color of the floss varies from location to location longitudinally or around its periphery, a color variation resulting from use of the floss will not be readily apparent. For this reason, the coating must be substantially uniform along the length of the floss as well as around the periphery of the floss.

The coating may be applied at an add-on typically ranging from about 10 percent to about 60 percent, preferably from about 20 percent to about 50 percent, based on the weight of the fiber substrate. The coating may be applied by processes known in the art, such as dip coating or spray coating for liquid coatings, and electrostatic deposition for dry coatings.

In producing the floss of the invention, the colorant-containing coating composition must be applied substantially uniformly to the surface of the floss to insure the uniformity of the distribution of coating on the surface. The coating must have approximately the same thickness along the length and around its circumference of the floss. In addition, it is critical that the colorant be distributed substantially uniformly within the coating. Together, these two factors provide a finished floss of uniform color. To achieve this uniformity of color on the floss, a coating process must used that precisely adheres a uniform coating thickness on the surface of the floss.

In a preferred embodiment, the equipment and process for making the floss of the invention is capable of doing the following:

1. Providing a coating composition in which the colorant is substantially uniformly distributed,
2. Maintaining the colorant in its substantially uniform distribution in the coating composition during all subsequent operations,
3. Pumping the coating composition in a uniform fashion into an application die,
4. Uniformly applying the coating composition to the yarn, and
5. Keeping the coating composition substantially undisturbed on the yarn until it is solidified intact.

The above-mentioned preferred process for making the floss of the invention is illustrated in FIG. 1. The first step in making the floss of the invention is to substantially uniformly disperse the colorant in the coating composition. The wax ingredient comprising this coating composition is liquefied if necessary, as by heating, and added to the mix tank 3. Next, colorant is added slowly to the liquefied ingredients while being stirred with a homogenizer 1 or through the use of a high sheer mixer 2 such as a Rotostat High Sheer Mixer Model #XPBL, made by Admix. Typically, a Rotosolver head blade is used in said high sheer mixer and is operated at, e.g., 1700 rpm. The coating mixture is mixed in this fashion for at least 15 minutes prior to adding other components.

Once the colorant has been uniformly mixed into the wax ingredient, the other components of the coating composition, such as spray dried flavor, saccharin, and other desired additives, are added. After the other components are thoroughly incorporated into the coating composition, the coating composition is kept uniformly mixed by a slower moving mixer blade (not shown in FIG. 1), typically operating at about 100 rpm. This speed is sufficient to keep the colorant particles in suspension, but not so fast as to stir air into the mixture.

The coating mixture is then allowed to flow into the positive displacement pump 4 which, when driven at a given speed, delivers a constant amount of coating. The positive displacement pump can be a vane type, piston pump, or similar type pump. No matter what type of pump is used, it is necessary to keep the solids, especially the colorant, in the mixture from settling out. This can be accomplished by keeping the flow velocities of the coating mixture sufficiently high to keep the materials in suspension or by providing agitation of the mixture through stirring or vibration.

The fiber substrate 20 is pulled off the end of a supply spool 6, and passes over a wheel 5, which drives a pulse counter (not shown in FIG. 1). The floss substrate is pulled through the process by rewinding the material on a take-up spool 21. The speed at which take-up spool 21 is operated is controlled by controller 11. Controller 11 may be a computer, a programmable logic controller or similar device. A signal is fed to controller 11 from the pulse counter driven by wheel 5 and the voltage of motor 10 is also controlled to maintain a constant velocity of the yarn. Electronic controller 11 also controls the speed of positive displacement pump 4. Thus the speed of the floss substrate is maintained while a constant amount of coating mixture is pumped into the coating die 7.

The coating die 7 contains at least two rollers 22, around which the floss substrate has at least some wrap. Generally, the floss wraps around the rollers at from 90° to 720°. The rollers assist in applying the coating mixture to the floss substrate as well as work the mixture in between fibers (where multi-filament yarns are being utilized). Downstream of the rollers there is a slot die region 23 where the coating mixture is smoothed onto the surface of the floss substrate. The slot die is in the form of a V-shaped groove having a radius at its bottom. As will be apparent to those skilled in the art, the dimensions of the V-shaped groove will depend upon such factors as the denier and type of fiber substrate and the amount of coating being applied thereto.

The coating composition applied to the fibrous substrate must be solidified. Solidification can be accomplished by having a open area 8 where the coating cools under ambient conditions or by use of a chamber where refrigerated or room air is blown over the floss to increase the rate of cooling. In order to avoid undesirable discontinuities in the coating, the floss should not contact any surfaces until the coating has solidified. Once the floss coating is cooled sufficiently to prevent any disruption of the outer surface, it is rewound on a standard rewind mechanism 9. This mechanism holds a core on a chuck, which is rotated as an eyelet is traversed back and forth along its length. Suitable traversing re-winders can be readily built or purchased from companies such as Leesona Corporation.

If it is desired to apply a second coating to the product, this may be done by locating another coating line and cooling chamber downstream of cooling area 8.

Several examples of the present invention are set forth below to further illustrate the nature of the invention and the manner of carrying it out. However, the invention should not be considered as being limited to the details thereof.

In the following Examples, the mentioned percentages are weight percentages.

EXAMPLE 1

A natural white color multifilament nylon yarn comprising 210 filaments (each filament having a denier of about 3) was coated in the above-described manner with a coating mixture consisting of microcrystalline wax (82.5%), a white colored spray dried flavor (17%) and red-colored Lake FD&C #30 (0.5%) of the kind described earlier herein. The white colored, spray dried flavor consisted of approximately 20% by weight of cinnamon oil dispersed in about 80% by weight of a modified starch. The coating was applied at levels of 35, 40 and 45% by weight of the yarn. In all cases, when the finished floss was used to floss the teeth, the portions of the colored coating which had contacted the teeth were disrupted but no readily discernible visual clue or signal was provided to the user. This was due to the fact that the coating applied to the fiber substrate gave a mottled appearance to the outer surface of the coated floss. When the coating composition was disrupted by flossing, the underlying white color of the fiber substrate which was thus exposed was difficult to readily distinguish from the mottled appearance of the outer coating. The aforementioned mottled appearance of the outer coating resulted from an insufficient concentration of the red-colored lake in the coating composition.

EXAMPLE 2

The natural white color multifilament nylon yarn used in Example 1 was coated with a coating mixture consisting of microcrystalline wax (82%), red-colored spray dried flavor (17%) and red-colored Lake FD&C #30 colorant (1%). The spray dried flavor consisted of approximately 20% by weight of cinnamon oil dispersed in about 80% by weight of a modified starch consisting of 98% by weight of modified starch and 2% by weight of red dye #40. The coating was applied at 35, 40 and 45% by weight of the multifilament yarn. In all cases, when the finished floss was used to floss the teeth, the coating on those portions of the floss which had contacted the teeth was disrupted and a visual clue or signal that the floss had been so used was provided to the user. This visual clue or signal resulted from the fact that the red color of the floss coating, when disrupted, exposed the natural white color of the underlying yarn substrate. The thus exposed natural white color of the underlying yarn was in sharp and easily noticeable contrast with the red color of the unused portions of the floss.

EXAMPLE 3

The natural white color multifilament nylon yarn used in Example 1 was coated with a mixture of microcrystalline wax (81%), red colored Lake FD&C #30 (2%) and white spray dried flavor (17%) consisting of approximately 20% cinnamon flavor oil and 80% modified starch. The coating was applied at 35, 40 and 45% by weight of the yarn. In all cases, when the finished floss was used to floss the teeth, the coating on those portions of the floss which had contacted the teeth was disrupted and a visual clue or signal that the floss had been so used was provided to the user displacement of the coating on the surface showed a visible color change in the area where it was displaced.

EXAMPLE 4

The natural color multifilament nylon yarn used in Example 1 was coated with a mixture of microcrystalline wax (86%) and white colored spray dried flavor (14%). The spray dried flavor consisted of 20% cinnamon flavor oil and 80% modified starch. This coating was applied at 25% by weight of the yarn and the resulting yarn was white in color. To this coated, white-colored yarn was uniformly applied a second coating composition consisting of PEG 1450 (98%) and red dye FD&C #40 (2%). The second coating, which was red in color, was applied at a rate that increased the weight of coated yarn by an additional 15%. Displacement of the red-colored outer coating on the surface of the floss during use revealed the underlying white color, thus providing a visual clue or signal that the floss had been used in those regions where the red colored coating was displaced.

What is claimed is:

1. A dental floss, comprising:
    a fiber substrate, said fiber substrate having a first color; said fiber substrate having a coating substantially uniformly applied thereto; said coating as applied to said fiber substrate comprising from about 0.1 to about 5 percent by weight of a second color which substantially completely masks said first color;
    whereby when said floss is contacted with teeth upon flossing, said coating is disrupted by said contact with the teeth to thereby reveal said first color.

2. The dental floss according to claim 1 wherein said fiber substrate is a monofilament.

3. The dental floss according to claim 1 wherein said fiber substrate is a multifilament.

4. The dental floss according to claim 1 wherein said fiber substrate is made from a polymer selected from the group consisting of nylon 6,6, nylon 6, polypropylene, polyester, polyethylene, and polytetrafluoroethylene.

5. The dental floss according to claim 1 wherein said coating is a soluble coating.

6. The dental floss according to claim 5 wherein said soluble coating is selected from the group consisting of low molecular weight polyethylene glycols.

7. The dental floss according to claim 5 wherein said coating comprises from about 0.1 to about 5 percent by weight of said second color.

8. The dental floss according to claim 5 wherein said coating comprises from about 0.75 to about 5 percent by weight of said second color.

9. The dental floss according to claim 1 wherein said coating is insoluble.

10. The dental floss according to claim 9 wherein said insoluble coating is selected from the group consisting of microcrystalline wax, beeswax, paraffin waxes and low molecular weight polyethylenes.

11. The dental floss according to claim 1 wherein said second color is provided by a Lake Pigment.

12. The dental floss according to claim 11 wherein said lake is a red-colored lake.

* * * * *